(12) United States Patent
Takahashi

(10) Patent No.: US 11,213,261 B2
(45) Date of Patent: Jan. 4, 2022

(54) RADIOGRAPHIC SYSTEM AND RADIOGRAPHIC METHOD

(71) Applicant: CANON KABUSHIKI KAISHA, Tokyo (JP)

(72) Inventor: Naoto Takahashi, Sagamihara (JP)

(73) Assignee: Canon Kabushiki Kaisha, Tokyo (JP)

(*) Notice: Subject to any disclaimer, the term of this patent is extended or adjusted under 35 U.S.C. 154(b) by 126 days.

(21) Appl. No.: 16/802,383

(22) Filed: Feb. 26, 2020

(65) Prior Publication Data

US 2020/0187883 A1 Jun. 18, 2020

Related U.S. Application Data

(63) Continuation of application No. PCT/JP2018/035018, filed on Sep. 21, 2018.

(30) Foreign Application Priority Data

Oct. 6, 2017 (JP) .............................. JP2017-196056

(51) Int. Cl.
*A61B 6/00* (2006.01)

(52) U.S. Cl.
CPC .......... *A61B 6/4233* (2013.01); *A61B 6/4266* (2013.01); *A61B 6/463* (2013.01); *A61B 6/5241* (2013.01); *A61B 6/5258* (2013.01)

(58) Field of Classification Search
CPC ... A61B 6/4233; A61B 6/4266; A61B 6/5241; A61B 6/5258; A61B 6/463; A61B 6/00; A61B 6/4283; A61B 6/52; A61B 6/5205
See application file for complete search history.

(56) References Cited

U.S. PATENT DOCUMENTS

| | | |
|---|---|---|
| 2016/0220213 A1 | 8/2016 | Miyamoto |
| 2016/0287202 A1 | 10/2016 | Miyachi |
| 2016/0302755 A1 | 10/2016 | Takagi |

FOREIGN PATENT DOCUMENTS

| | | | | |
|---|---|---|---|---|
| EP | 1231484 A2 * | 8/2002 | ........... | G01T 1/2014 |
| JP | 2002-044413 A | 2/2002 | | |
| JP | 2010-39267 A | 2/2010 | | |
| JP | 2011-188972 A | 9/2011 | | |
| JP | 2016-106795 A | 6/2016 | | |
| JP | 2016-140509 A | 8/2016 | | |
| JP | 2016-140515 A | 8/2016 | | |
| JP | 2016-189982 A | 11/2016 | | |
| JP | 2016-198424 A | 12/2016 | | |
| JP | 2017-94131 A | 6/2017 | | |

* cited by examiner

*Primary Examiner* — Don K Wong

(74) *Attorney, Agent, or Firm* — Canon U.S.A., Inc. IP Division

(57) ABSTRACT

Provided are a radiographic system and a radiographic method that enable appropriate correction of an area including an imaged structure in the case in which radiation detection apparatuses of different inner structures exist together and consequently achieve improvement of the image quality of a composite image. The radiographic system according to the present invention includes an image corrector that corrects an area of a composite image in which the structure of a radiation detection apparatus is imaged. The image corrector sets a correction method in accordance with a characteristic of a structural shadow of the radiation detection apparatus imaged in the composite image.

13 Claims, 9 Drawing Sheets

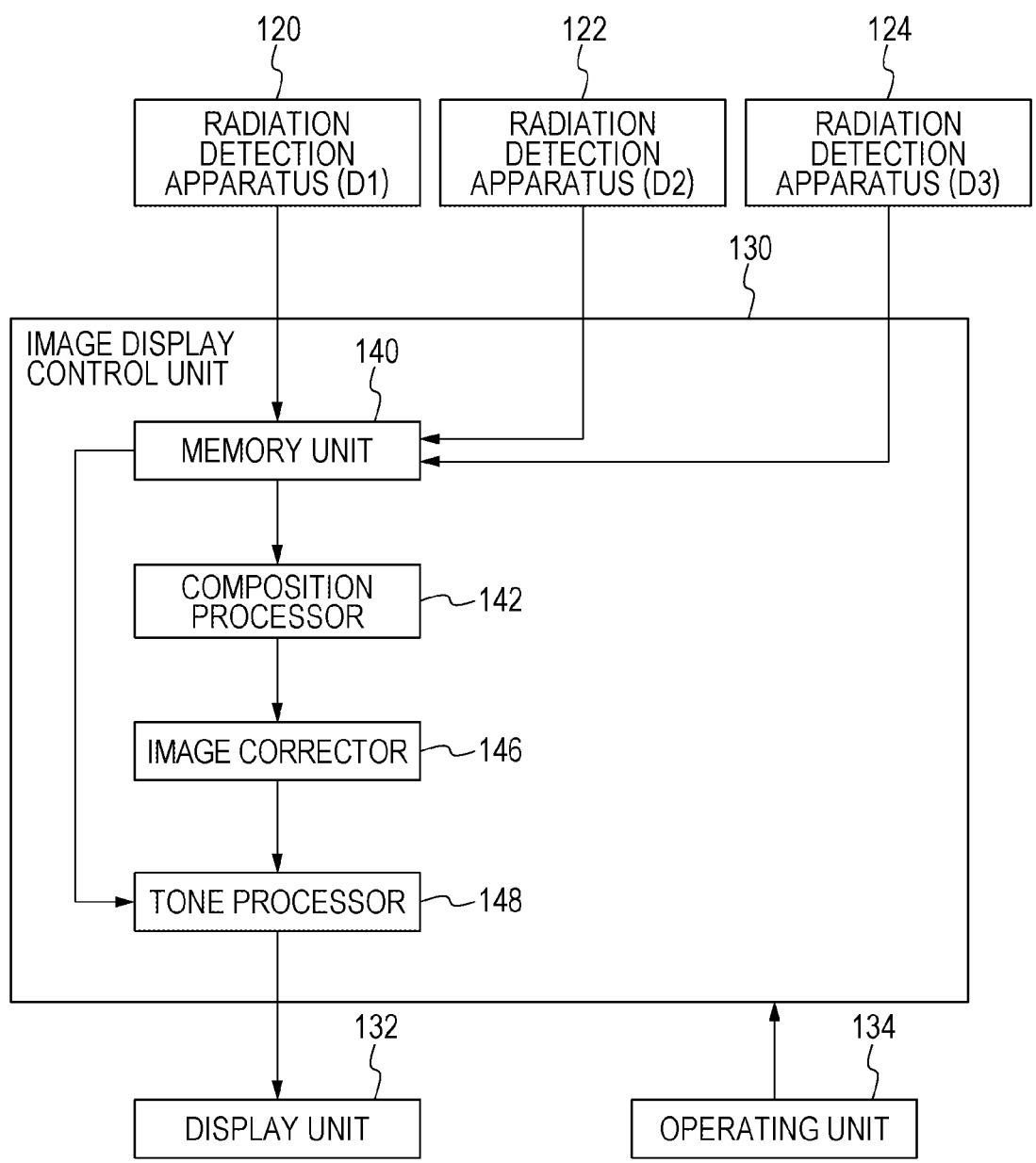

RADIOGRAPHIC SYSTEM AND RADIOGRAPHIC METHOD

CROSS-REFERENCE TO RELATED APPLICATIONS

This application is a Continuation of International Patent Application No. PCT/JP2018/035018, filed Sep. 21, 2018, which claims the benefit of Japanese Patent Application No. 2017-196056, filed Oct. 6, 2017, both of which are hereby incorporated by reference herein in their entirety.

TECHNICAL FIELD

The present invention relates to a radiographic system and a radiographic method that are used for image capturing by utilizing radiation rays.

BACKGROUND ART

In recent years, in the medical field, image capturing for wide observation areas (hereinafter referred to as long-length imaging), such as imaging the entire spinal column or an entire lower limb of an examinee has been practiced. PTL 1 discloses long-length imaging achieved by performing imaging with the use of a plurality of radiation detection apparatuses that are arranged adjacent to each other, in which correction is performed for a particular part of a long-length image (also referred to as a composite image) in which the structure of a radiation detection apparatus of the radiation detection apparatuses arranged in an overlapping manner is imaged in the particular part. Furthermore, PTL 2 discloses a method in which the structure of radiation detection apparatus is modified to reduce the part in which the structure of a radiation detection apparatus of the radiation detection apparatuses arranged in an overlapping manner is imaged.

CITATION LIST

Patent Literature

PTL 1 Japanese Patent Laid-Open No. 2016-140515
PTL 2 Japanese Patent Laid-Open No. 2017-94131

Radiation detection apparatuses of various inner structures are used for long-length imaging; for example, a radiation detection apparatus of a simplified structure as in PTL 2 or a radiation detection apparatus of a complex structure is utilized. As a result, the type of correction operation for composite images varies depending on the structural shadow captured in a long-length image. However, PTL 1 and 2 do not mention any measure against the case in which radiation detection apparatuses of various inner structures exist together.

An object of the present invention is to provide a radiographic system and a radiographic method that enable appropriate correction of composite images in the case in which radiation detection apparatuses of different inner structures exist together.

SUMMARY OF INVENTION

To achieve an object of the present invention, a radiographic system includes a plurality of radiation detection apparatuses that each detect radiation rays, a composition processor that composites a plurality of radiographic images obtained from the plurality of radiation detection apparatuses and generates a composite image, and an image corrector that corrects an area of the composite image, the area including an imaged structure of a radiation detection apparatus of the plurality of radiation detection apparatuses, and that sets a correction method in accordance with a characteristic of a structural shadow of the radiation detection apparatus imaged in the composite image.

Further features of the present invention will become apparent from the following description of exemplary embodiments with reference to the attached drawings.

BRIEF DESCRIPTION OF DRAWINGS

FIG. 3 is a diagram schematically illustrating a configuration of the radiographic system (mainly an image display control unit) of the present invention.

DESCRIPTION OF EMBODIMENTS

Hereinafter, embodiments of the present invention will be described with reference to the accompanying drawings.

First Embodiment

Figure 1:
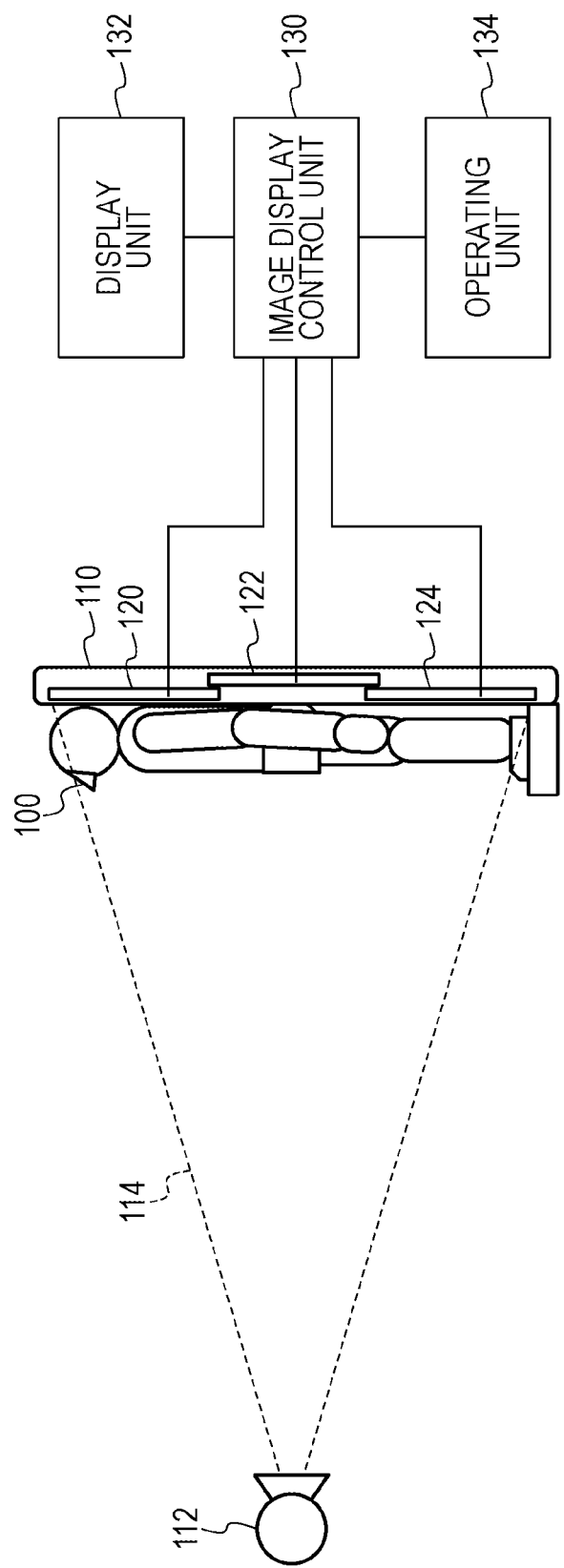
FIG. 1 is a diagram schematically illustrating a configuration of a radiographic system of the present invention.

FIG. 1 is a diagram schematically illustrating a configuration of a radiographic system used for long-length imaging performed by a plurality of radiation detection apparatuses that are arranged adjacent to each other.

The radiographic system includes a radiation generator 112 that generates radiation rays. The radiation generator 112 can irradiate an irradiation range 114 with radiation rays. The radiation generator 112 is installed by using a supporting member (not illustrated in the drawing) positioned at a floor or a ceiling. A diaphragm (not illustrated in the drawing) that blocks radiation rays is positioned at a radiation plane of the radiation generator 112. By controlling the diaphragm that blocks radiation rays, an operator can set the irradiation range 114 of radiation rays applied by the radiation generator 112.

The radiographic system includes a plurality of radiation detection apparatuses 120, 122, and 124. While the form constituted by the three radiation detection apparatuses 120, 122, and 124 is described here, two, four, or more radiation detection apparatuses may be used. The plurality of radiation detection apparatuses 120, 122, and 124 each detect radiation rays having passed through an examinee 100 and outputs image data representing the radiation rays. The image data can be reworded as a radiographic image.

Specifically, the plurality of radiation detection apparatuses 120, 122, and 124 detect, as electric charge equivalent to the amount of radiation, radiation rays having passed through an examinee. For example, the plurality of radiation detection apparatuses 120, 122, and 124 each use a direct conversion sensor that directly converts radiation rays into electric charge, such as a sensor using, for example, a-Se that converts radiation into electric charge, or an indirect sensor using a scintillator, such as CsI, and a photoelectric conversion element of, for example, a-Si. The plurality of radiation detection apparatuses 120, 122, and 124 generate image data by performing analog-to-digital (A/D) conversion for the detected electric charge and outputs the image data to an image display control unit 130.

The plurality of radiation detection apparatuses 120, 122, and 124 are accommodated in an imaging stand 110. The imaging stand 110 is a rectangular housing of a hollow structure. The imaging stand 110 has a function of holding the plurality of radiation detection apparatuses 120, 122, and 124. As illustrated in FIG. 1, the imaging stand 110 is positioned to stand upright relative to the floor. The examinee 100 is positioned in a longitudinal direction of the imaging stand 110. The imaging stand 110 has a function of supporting the examinee 100.

In FIG. 1, the imaging stand 110 is positioned such that the longitudinal direction of the imaging stand 110 is directed in the vertical direction, that is, the imaging stand 110 stands upright relative to the floor. The imaging stand 110 may be positioned such that the longitudinal direction of the imaging stand 110 is directed in the horizontal direction, that is, the imaging stand 110 may be positioned in parallel with the floor.

In the imaging stand 110, the radiation detection apparatuses 120, 122, and 124 are arranged in the longitudinal direction of the imaging stand 110.

The plurality of radiation detection apparatuses each are positioned such that part of the particular radiation detection apparatus overlaps part of another radiation detection apparatus. For example, as illustrated in FIG. 1, the radiation detection apparatuses 120 and 122 are arranged to partially overlap in terms of spatial relationship. In this arrangement, the imaging area of the radiation detection apparatus 120 and the imaging area of the radiation detection apparatus 122 overlap. Similarly, the radiation detection apparatuses 122 and 124 are arranged to partially overlap in terms of spatial relationship. In this arrangement, the imaging area of the radiation detection apparatus 122 and the imaging area of the radiation detection apparatus 124 overlap. The radiation detection apparatus 122 is positioned on the back side of the radiation detection apparatus 120 and the back side of the radiation detection apparatus 124; in other words, the radiation detection apparatus 122 is positioned further from the radiation generator 112 than the radiation detection apparatuses 120 and 124.

The radiographic system further includes the image display control unit 130, a display unit 132, and an operating unit 134. The image display control unit 130 performs image processing for the image data outputted by the radiation detection apparatus and generates an image. The display unit 132 displays the image. The operating unit 134 is used by the operator to provide instructions. The image display control unit 130 has a function of controlling each component.

The image display control unit 130 is coupled to the plurality of radiation detection apparatuses 120, 122, and 124. Specifically, the image display control unit 130 is coupled to the plurality of radiation detection apparatuses 120, 122, and 124 by using a wired or wireless network or dedicated lines. The plurality of radiation detection apparatuses 120, 122, and 124 each image radiation rays generated by the radiation generator 112 and output image data to the image display control unit 130. The image display control unit 130 has a function of an application that runs on a computer. While the image display control unit 130 controls operations of the plurality of radiation detection apparatuses 120, 122, and 124, the image display control unit 130 outputs an image to the display unit 132 and outputs a graphical user interface (not illustrated in the drawing).

The image display control unit 130 controls the time at which the radiation generator 112 generates radiation rays and imaging conditions of radiation rays. The image display control unit 130 also controls the time at which the plurality of radiation detection apparatuses 120, 122, and 124 perform image capturing to obtain image data and the time at which the plurality of radiation detection apparatuses 120, 122, and 124 output the image data. The image display control unit 130 can cause the plurality of radiation detection apparatuses 120, 122, and 124 to simultaneously perform image capturing and simultaneously output image data.

The image display control unit 130 has a function of performing image processing such as tone conversion for the image data outputted by the plurality of radiation detection apparatuses 120, 122, and 124. The image display control unit 130 can also perform image processing such as cropping or rotating for the image outputted by the plurality of radiation detection apparatuses 120, 122, and 124. The display unit 132 displays the image outputted by the image display control unit 130.

The examinee 100 stands on a stage placed at the imaging stand 110 and is subjected to positioning with respect to the plurality of radiation detection apparatuses 120, 122, and 124, and the radiation generator 112. In the present embodiment, radiation rays are emitted at an angle that enables the radiation rays to be directed perpendicularly to the center of the radiation detection apparatus 122. Radiation rays are emitted by the radiation generator 112 toward the plurality of radiation detection apparatuses 120, 122, and 124, pass through the examinee 100, and consequently reach the plurality of radiation detection apparatuses 120, 122, and 124 and are detected. The image data obtained by the plurality of radiation detection apparatuses 120, 122, and 124 is subjected to composition processing by the image display control unit 130 and a composite image of the examinee 100 is accordingly generated. The composite image is obtained by performing long-length imaging in which the observation area is relatively wide. The display unit 132 displays the composite image outputted by the image display control unit 130.

The radiographic system of the present invention can perform long-length imaging to image the entire spinal column or both the lower limbs of the examinee 100 by performing radiation one time. The radiation rays (the irradiation range 114) emitted by the radiation generator 112 are simultaneously applied to the plurality of radiation detection apparatuses 120, 122, and 124. For example, the operator controls the diaphragm that blocks radiation rays or adjusts the distance between the radiation generator 112 and the plurality of radiation detection apparatuses 120, 122, and 124.

The plurality of radiation detection apparatuses 120, 122, and 124 each may have a function of automatically detecting irradiation with radiation rays performed by the radiation generator 112. The function of automatically detecting irradiation is a function with which, when the radiation generator 112 emits the radiation rays, the plurality of radiation detection apparatuses 120, 122, and 124 detect radiation rays and the electric charge due to the radiation rays is built up in the plurality of radiation detection apparatuses 120, 122, and 124. When any one of the plurality of radiation detection apparatuses 120, 122, and 124 detects irradiation with radiation rays, the plurality of radiation detection apparatuses 120, 122, and 124 starts actual read operation and obtains image data.

In the radiographic system described above, the radiation detection apparatus 122 is positioned to overlap the radiation detection apparatuses 120 and 124 at the back of the radiation detection apparatus 120 and the back of the radiation detection apparatus 124. As a result, the image data outputted by the radiation detection apparatus 122 includes an area (hereinafter referred to as a defective region) including the image of a structure, such as a radiation detection panel, a board, or a housing, that is an inner component of the radiation detection apparatus 120 and such an area of the radiation detection apparatus 124.

Figure 2A:
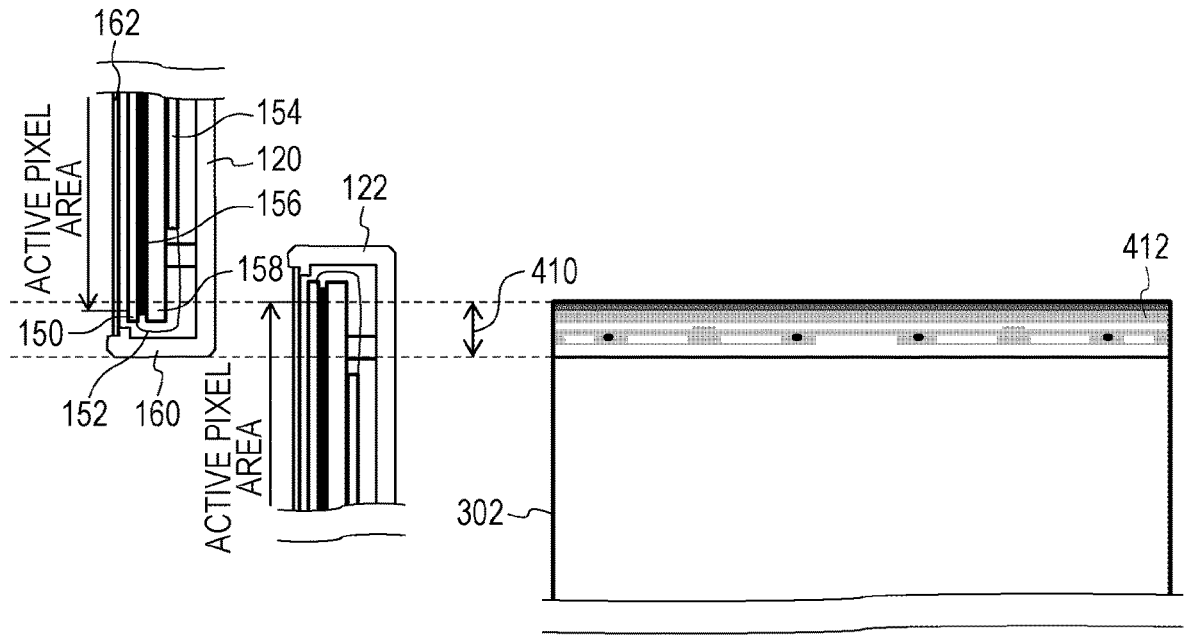
FIG. 2A illustrates a relationship between radiation detection apparatuses of the radiographic system of the present invention and image data.

A mechanism of occurrence of this defective region is described with reference to FIGS. 2A and 2B. FIG. 2A illustrates an example of an inner structure of the radiation detection apparatus 120 and an inner structure of the radiation detection apparatus 122. The radiation detection apparatus 120 involves a coupling body in which, listed in order starting with the one at the radiation-entrance-plane side, a radiation detection panel 150 that detects radiation rays, an adhesive material 156 that is used to cause the radiation detection panel 150 to adhere to a panel base 158, the panel base 158 that supports the radiation detection panel 150, and a control board 154 that controls the radiation detection panel 150 to output electrical signals are layered. The radiation detection panel 150 and the control board 154 are coupled to each other via a flexible circuit board 152.

An outer housing of the radiation detection apparatus 120 is constituted by an outer housing 160 formed of a metal or carbon and a radiation-transmissive member 162 formed of a radiation-transmissive material that enables transmission of radiation rays. The radiation-transmissive member 162 is positioned at the radiation entrance plane of the radiation detection panel 150, so that the attenuation of radiation rays emitted by the radiation generator 112 is suppressed. The radiation detection panel 150 has an active pixel area in which radiation rays are detectable and an edge part outside the periphery of the active pixel area.

The radiation detection apparatus 122 is positioned such that the active pixel area of the radiation detection apparatus 122 partially overlaps the active pixel area of the radiation detection apparatus 120 and image information is reliably obtained with respect to any line by either the active pixel area of the radiation detection apparatus 120 or the active pixel area of the radiation detection apparatus 122. A composite image is generated on the basis of both the image data (a radiographic image) outputted by the radiation detection apparatus 120 and the image data (a radiographic image) of an image area that is not included in the image data obtained by the radiation detection apparatus 120 but that is included in the image data outputted by the radiation detection apparatus 122.

Here, a structure of the radiation detection apparatus 120 is captured in image data 302 obtained by the radiation detection apparatus 122. An area 410 extending from an end of the active pixel area of the radiation detection apparatus 122 to an end of the outer housing of the radiation detection apparatus 122 is an area in which a structure of the radiation detection apparatus 122 is captured in the image data obtained by the radiation detection apparatus 122. A defective region 412 including an imaged structure of the radiation detection apparatus 120 appears in the image data 302 obtained by the radiation detection apparatus 122. In a composition processor 142, the defective region 412 appears in the same manner in a composite image generated from the image data 302 obtained from the radiation detection apparatus 122.

In the defective region 412 of the image data 302 obtained by the radiation detection apparatus 122, the radiation detection panel 150, the flexible circuit board 152, the adhesive material 156, the panel base 158, and the outer housing 160 of the radiation detection apparatus 120 are partially imaged as a structural shadow. Additionally, in the defective region 412, a structural shadow caused by a board and a screw in the flexible circuit board 152 is included.

As described above, the defective region is an area including the image of a structural shadow caused by the inner structure of the radiation detection apparatus positioned in front. In the defective region, the structural shadow may overlap the shadow of an examinee and this may obstruct diagnoses.

The structural shadow considerably changes depending on the inner structure of the radiation detection apparatus. For example, by modifying the inner structure, the radiation detection apparatus 120 illustrated in FIG. 2B achieves simplification and reduction of the structural shadow in comparison to FIG. 2A.

Figure 2B:
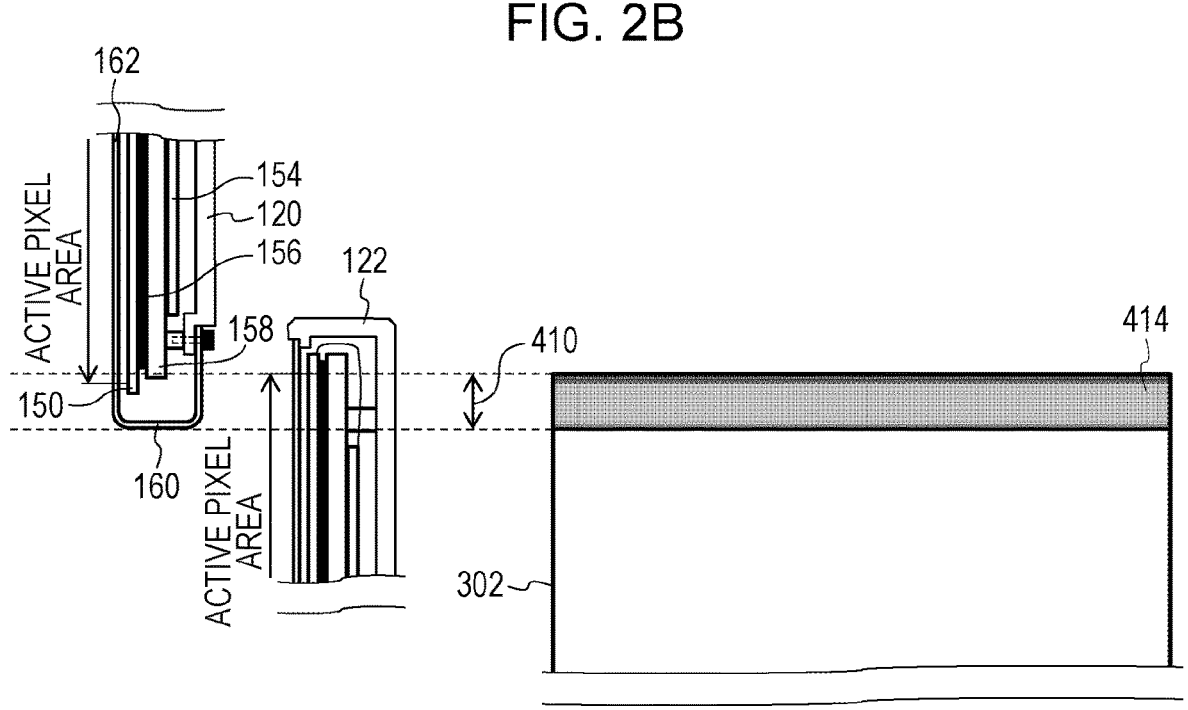
FIG. 2B illustrates another relationship between the radiation detection apparatuses of the radiographic system of the present invention and image data.

Specifically, in the radiation detection apparatus 120 illustrated in FIG. 2B, reduction of the structural shadow is achieved by changing the outer housing 160 from a metal housing to a radiation-transmissive housing by which attenuation of radiation rays can be suppressed. Furthermore, the adhesive material 156 and the panel base 158 are positioned inside not to overlap the active pixel area of the radiation detection apparatus 122, and as a result, imaging the adhesive material 156 and the panel base 158 in the active pixel area is hindered. Moreover, a flexible circuit board and a screw (not illustrated in the drawing) are positioned not to overlap the active pixel area, and as a result, imaging a complex structural shadow caused by the board and the screw is hindered.

In this manner, a defective region 414 in the image data 302 obtained by the radiation detection apparatus 122 is mainly constituted by the radiation detection panel 150 and the outer housing 160 and the structural shadow of the defective region 414 indicates a simple structure. In addition, the amount of attenuation of radiation rays caused by the inner structure is relatively small, and thus, the contrast of the structural shadow is lowered.

There are various inner structures other than the inner structure of the radiation detection apparatus illustrated in FIG. 2. A radiation detection apparatus has different inner structures between the upper end and the lower end of the radiation detection apparatus. For example, in one case, the image data 302 includes an area including the image of the structural shadow as illustrated in FIG. 2A due to the upper end of the radiation detection apparatus. This means that the defective region 412 including an imaged structure of the radiation detection apparatus 120 appears in the image data 302 obtained by the radiation detection apparatus 122. In one case, the image data 302 includes an area including the image of the structural shadow as illustrated in FIG. 2B due to the lower end of the radiation detection apparatus. This means that the defective region 414 including an imaged structure of the radiation detection apparatus 120 appears in the image data 302 obtained by the radiation detection apparatus 122.

Next, with reference to a configuration diagram of the radiographic system of the present invention illustrated in FIG. 3, a manner in which a defective region of a composite image caused by an overlap between radiation detection apparatuses described above is corrected to improve the image quality is described.

The image display control unit 130 includes a memory unit 140 that stores image data outputted by the radiation detection apparatuses, the composition processor 142 that composites items of image data and generates a composite image, an image corrector 146 that corrects a defective region in a composite image to render the defective region inconspicuous, and a tone processor 148 that performs tone processing for the composite image having been corrected by the image corrector 146.

The memory unit 140 stores image data (radiographic images) outputted by the plurality of radiation detection apparatuses 120, 122, and 124. As illustrated in FIG. 3, the radiation detection apparatuses 120, 122, and 124 are indicated as a radiation detection apparatus (D1), a radiation detection apparatus (D2), and a radiation detection apparatus (D3).

The memory unit 140 can store image data outputted by the radiation detection apparatuses 120, 122, and 124 together with time information. As a result, the memory unit 140 can determine whether particular radiographic images outputted by the radiation detection apparatuses 120, 122, and 124 have been simultaneously obtained and store the radiographic images by using information of time at which each radiographic image was obtained. The memory unit 140 stores radiographic images in a manner in which a radiographic image including image information of an examinee and a radiographic image not including image information of an examinee are distinguished from each other.

The memory unit 140 can store a plurality of radiographic images simultaneously captured by the plurality of radiation detection apparatuses 120, 122, and 124 in association with position information (spatial-placement information) of the radiation detection apparatuses. For example, the memory unit 140 can store, in an associated manner, information indicating that particular image data outputted by the radiation detection apparatus 120 and particular image data outputted by the radiation detection apparatus 122 are of images adjacent to each other. Similarly, the memory unit 140 can store, in an associated manner, information indicating that particular image data outputted by the radiation detection apparatus 122 and particular image data outputted by the radiation detection apparatus 124 are of images adjacent to each other. Additionally, the memory unit 140 can store, in an associated manner, information indicating that the radiation detection apparatus 122 is positioned on the back side of the radiation detection apparatus 120 and the back side of the radiation detection apparatus 124. The memory unit 140 can output a plurality of items of image data and the position information about the items of image data to the composition processor 142.

The memory unit 140 can also store identification information (identification codes) for identifying the radiation detection apparatuses 120, 122, and 124. The identification code includes information indicating the type of a particular radiation detection apparatus; in other words, the identification code is information for indicating the inner structure of a particular radiation detection apparatus and includes information corresponding to a structural shadow (an image of a structure) of a particular radiation detection apparatus. The identification code may include information based on position information (placement information) of a particular radiation detection apparatus in addition to the type of the radiation detection apparatus. The position information (placement information) of a radiation detection apparatus includes, for example, information indicating the position of the radiation detection apparatus in the imaging stand 110 and information indicating the position of the upper end and the position of the lower end of the radiation detection apparatus. The position information (placement information) of a radiation detection apparatus may include information indicating the top-to-bottom orientation of the radiation detection apparatus. Thus, by using the identification code, it is possible to identify a structural shadow captured in image data obtained by a radiation detection apparatus positioned on the back side.

As described above, by using the identification code, for example, it is possible to distinguish between the radiation detection apparatus 120 illustrated in FIG. 2A and the radiation detection apparatus 120 illustrated in FIG. 2B. By using the identification code, it is possible to determine which kind of area the image data 302 includes: an area including the image of the structural shadow as illustrated in FIG. 2A or an area including the image of the structural shadow as illustrated in FIG. 2B.

The composition processor 142 composites a plurality of items of image data stored in the memory unit 140 and consequently generates a composite image. At this time, the composition processor 142 composites a plurality of items of image data including image information of the examinee 100 and generates a composite image.

The composition processor 142 generates a composite image by performing composition on the basis of a plurality of items of image data outputted by the radiation detection apparatuses 120, 122, and 124, and corresponding time information and position information. Specifically, the composition processor 142 determines as composition targets a plurality of items of image data (radiographic images) that have been simultaneously outputted by the radiation detection apparatuses 120, 122, and 124 in accordance with time information and composites the plurality of items of image data. The composition processor 142 determines a positional relationship of the plurality of items of image data outputted by the radiation detection apparatuses 120, 122, and 124 in accordance with position information and performs composition. Here, an identification code for identifying a particular structural shadow that is present in a defective region of the composite image is stored as supplementary information of the composite image.

For example, in the example illustrated in FIG. 1, the image data outputted by the radiation detection apparatus 120 is positioned on the upper side; the image data outputted by the radiation detection apparatus 124 is positioned on the lower side; and the image data outputted by the radiation detection apparatus 122 is positioned between those items of image data. Additionally, the composition operation is performed in consideration of the overlapping mode indicated by position information. For example, defective regions appear on the upper side and the lower side of the radiation detection apparatus 122 that is positioned further from the radiation generator 112 than the other radiation detection apparatuses and that overlaps the other radiation detection apparatuses. No defective region appears in the radiation detection apparatuses 120 and 124. Thus, the composition processor 142 can minimize the size of a defective region appearing in a composite image by generating the composite image by using image data generated by the radiation detection apparatuses 120 and 124 for the ranges in which the radiation detection apparatuses overlap. As described above, the composition processor 142 can generate a composite image by compositing a plurality of items of image data obtained by performing image capturing for a plurality of imaging areas adjacent to each other.

Identification codes for identifying structural shadows in defective regions appearing on the upper side and the lower side of image data are stored as supplementary information together with a corresponding composite image. For example, the composition processor 142 (the image display control unit 130) stores the identification codes together with the composite image. For example, when the inner structure of the radiation detection apparatus 120 indicated in FIG. 1 is the same as the inner structure of the radiation detection apparatus 120 illustrated in FIG. 2A, the structural shadow imaged in a defective region in a composite image is the same as the structural shadow in the defective region 412 illustrated in FIG. 2A. Thus, a unique identification indicating this structural shadow is stored as supplementary information. Similarly, when the inner structure of the radiation detection apparatus 124 indicated in FIG. 1 is the same as the inner structure of the radiation detection apparatus 120 illustrated in FIG. 2B, the structural shadow imaged in a defective region in a composite image is the same as the structural shadow in the defective region 414 illustrated in FIG. 2B.

The image corrector 146 corrects, in accordance with structural information, the defective region in the composite image outputted by the composition processor 142. The structural information is information representing a structural shadow imaged in a defective region. In the present embodiment, particular structural data is also used as the structural information. The structural data is obtained by performing image capturing by using a plurality of radiation detection apparatuses that are arranged in an overlapping manner in the state in which no examinee is present. This structural data includes an image in which the inner structure of a radiation detection apparatus is captured. The pixel value regarding this image is determined, for example, such that the value of a pixel is relatively small when the image of a thick structure of a relatively large radiation attenuation coefficient is captured in the pixel; the value of a pixel is relatively large when the image of a thin structure of a relatively small radiation attenuation coefficient is captured in the pixel.

Figure 4:
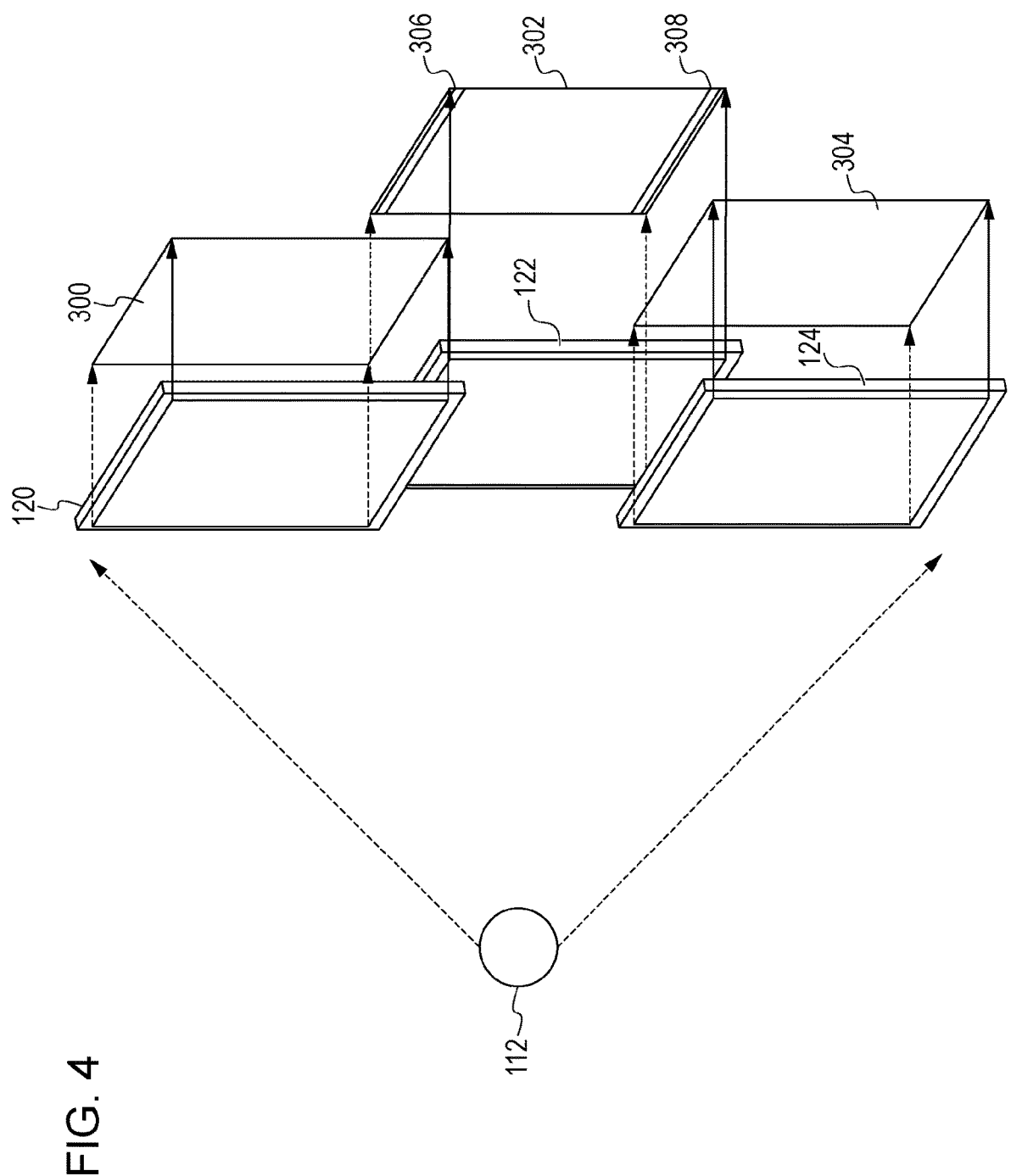
FIG. 4 illustrates a method of obtaining structural data in the radiographic system of the present invention.

The structural data is obtained in advance and stored in the memory unit 140. For example, in the case in which image capturing is to be performed for an examinee with the arrangement of the radiation detection apparatuses illustrated in FIG. 1, the radiation detection apparatuses 120, 122, and 124 are arranged as illustrated in FIG. 4 in the same manner as in FIG. 1 and image capturing is performed without any examinee. The image data 302 obtained from the radiation detection apparatus 122 by performing image capturing in this manner includes a capture area 306 of the inner structure at the lower end of the radiation detection apparatus 120 that overlaps the radiation detection apparatus 122. Similarly, the image data 302 obtained by the radiation detection apparatus 122 includes a capture area 308 of the inner structure at the upper end of the radiation detection apparatus 124 that overlaps the radiation detection apparatus 122.

Image data (a radiographic image) 300 obtained by the radiation detection apparatus 120 do not include any area including an imaged structure of another radiation detection apparatus. Similarly, image data (a radiographic image) 304 obtained by the radiation detection apparatus 124 do not include any area including an imaged structure of another radiation detection apparatus. Thus, the image data 302 corresponds to structural data representing a structural shadow captured in an image and the image data 302 can be stored as structural data in the memory unit 140. It should be noted that, the capture area 306 at the upper end and the capture area 308 at the lower end may be retained while being deemed to be different items of structural data.

The tone processor 148 performs tone processing for a composite image obtained by compositing a plurality of items of image data (radiographic images). Specifically, the tone processor 148 obtains from the memory unit 140 a plurality of items of image data obtained by the radiation detection apparatuses 120, 122, and 124. The tone processor 148 analyzes features of each of the plurality of items of image data obtained by the radiation detection apparatuses 120, 122, and 124 and determines a tone conversion characteristic for a composite image so that the dynamic range of the display unit 132 is effectively utilized.

Subsequently, the tone processor 148 converts the tone of the composite image by using the determined tone conversion characteristic. The features include, with respect to each item of image data, a histogram, a maximum pixel value, and a minimum pixel value. The features are calculated by performing analysis processing for a plurality of items of image data obtained by the radiation detection apparatuses 120, 122, and 124.

The tone processor 148 performs tone processing for the composite image having been corrected by the image corrector 146. Since tone processing is performed for a composite image in which a defective region has been reduced, it is possible to appropriately perform tone processing for the composite image. This means that the tone processor 148 can perform tone processing for a composite image in the state in which the effect of the imaged structure of the radiation detection apparatus 120 and the effect of the imaged structure of the radiation detection apparatus 124 are reduced. The display unit 132 displays the composite image having been subjected to tone processing by the tone processor 148.

Figure 5:
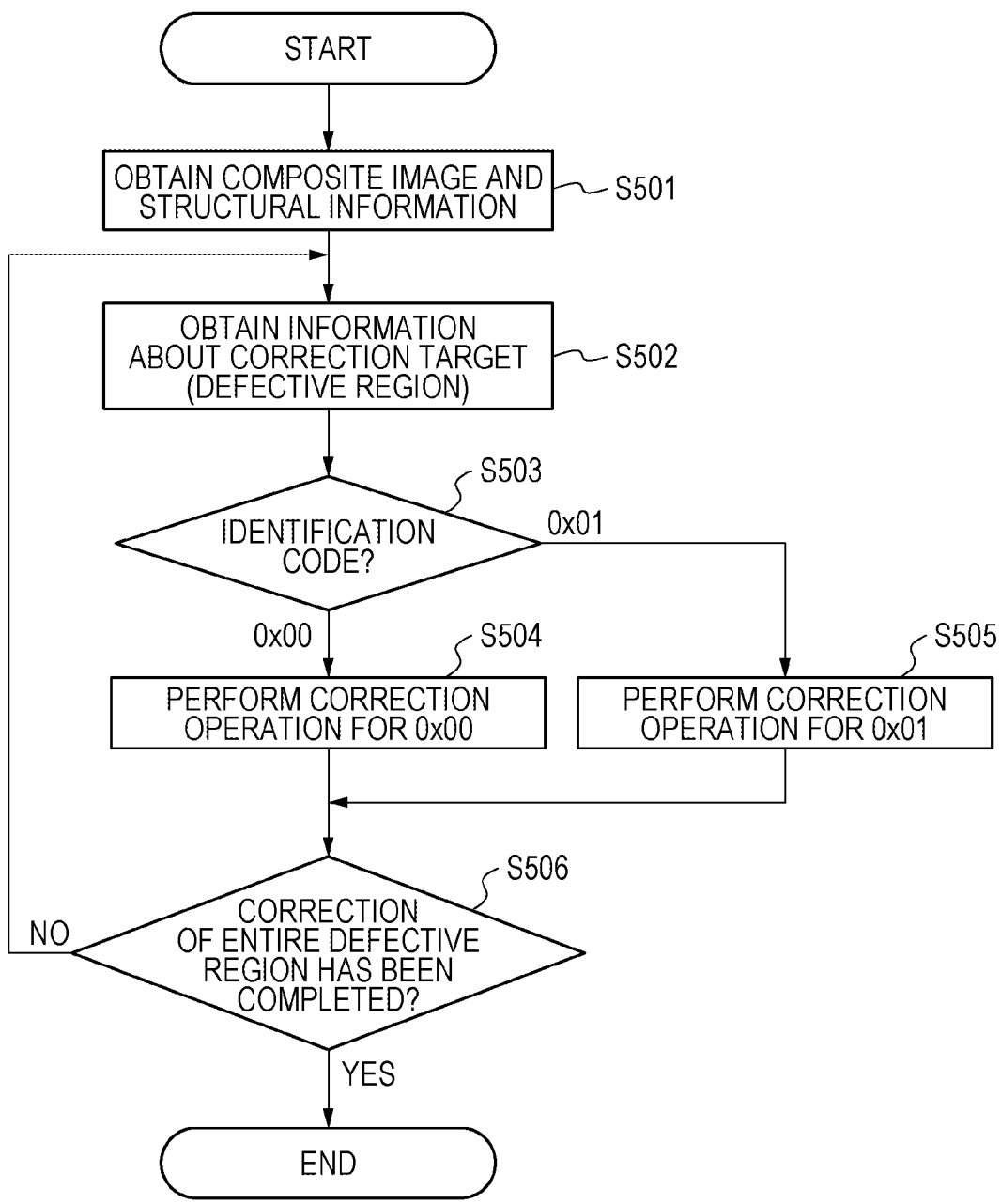
FIG. 5 is a flowchart illustrating a processing procedure of an image corrector of a first embodiment of the present invention.

Next, an operational procedure of the image corrector 146 that is a feature element of the radiographic system of the present embodiment is described in detail with reference to a flowchart in FIG. 5.

As described above, the composition processor 142 determines a positional relationship of the plurality of items of image data outputted by the radiation detection apparatuses 120, 122, and 124 in accordance with position information and performs composition. Additionally, identification information (an identification code) for identifying a particular structural shadow that is present in a defective region of the composite image is stored as supplementary information of the composite image.

The image corrector 146 obtains from the composition processor 142 a composite image and an identification code regarding a structural shadow imaged in a defective region as structural information (S501). Since the identification code according to the present embodiment includes information of the type of a radiation detection apparatus and information based on position information (placement information) of the radiation detection apparatus, the identification code enables identification of the form (the structural shadow) of a defective region in a composite image.

Here, it is assumed that the radiation detection apparatus 120 and the radiation detection apparatus 124 according to the present embodiment differ from each other in terms of the inner structure. Specifically, it is assumed that the radiation detection apparatus 120 has an inner structure identical to the inner structure of the radiation detection apparatus 120 illustrated in FIG. 2B. It is also assumed that the inner structure of the radiation detection apparatus 124 is identical to the inner structure of the radiation detection apparatus 120 illustrated in FIG. 2A.

Figure 6:
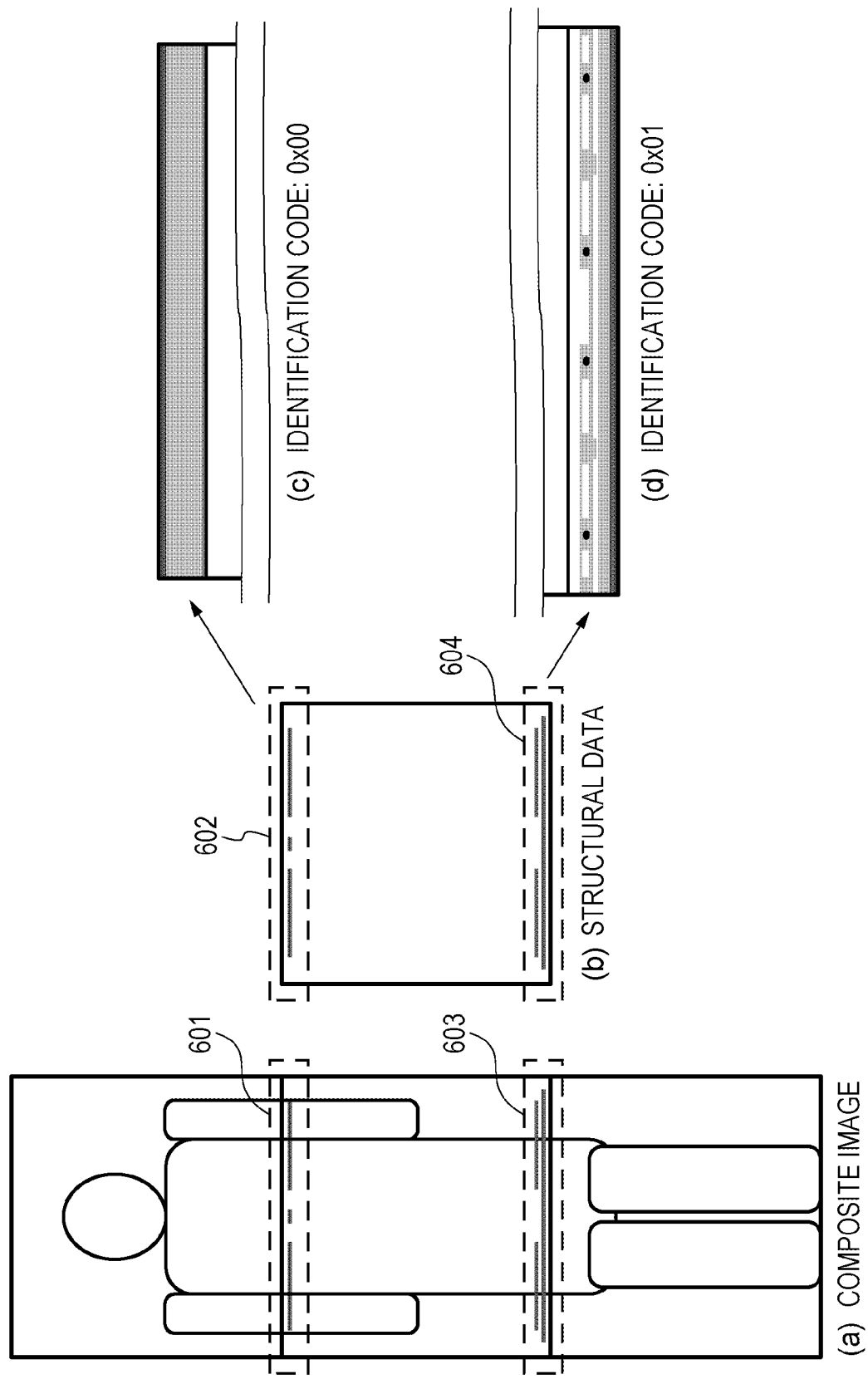
FIG. 6 illustrates a composite image and structural information of the first embodiment of the present invention.

As a result, a composite image in the present embodiment includes two different structural shadows. Specifically, a simple structure as illustrated in (c) of FIG. 6 at which the amount of attenuation of radiation rays is relatively small is captured in a defective region 601 that is present at an upper part of the composite image. By contrast, a complex structure as illustrated in (d) of FIG. 6 at which the amount of attenuation of radiation rays is relatively large is captured in a defective region 603 that is present at a lower part of the composite image. In the following description, it is assumed that the identification code of the structural shadow illustrated in (c) of FIG. 6 is 0x00 and the identification code of the structural shadow illustrated in (d) of FIG. 6 is 0x01.

Figure 7:
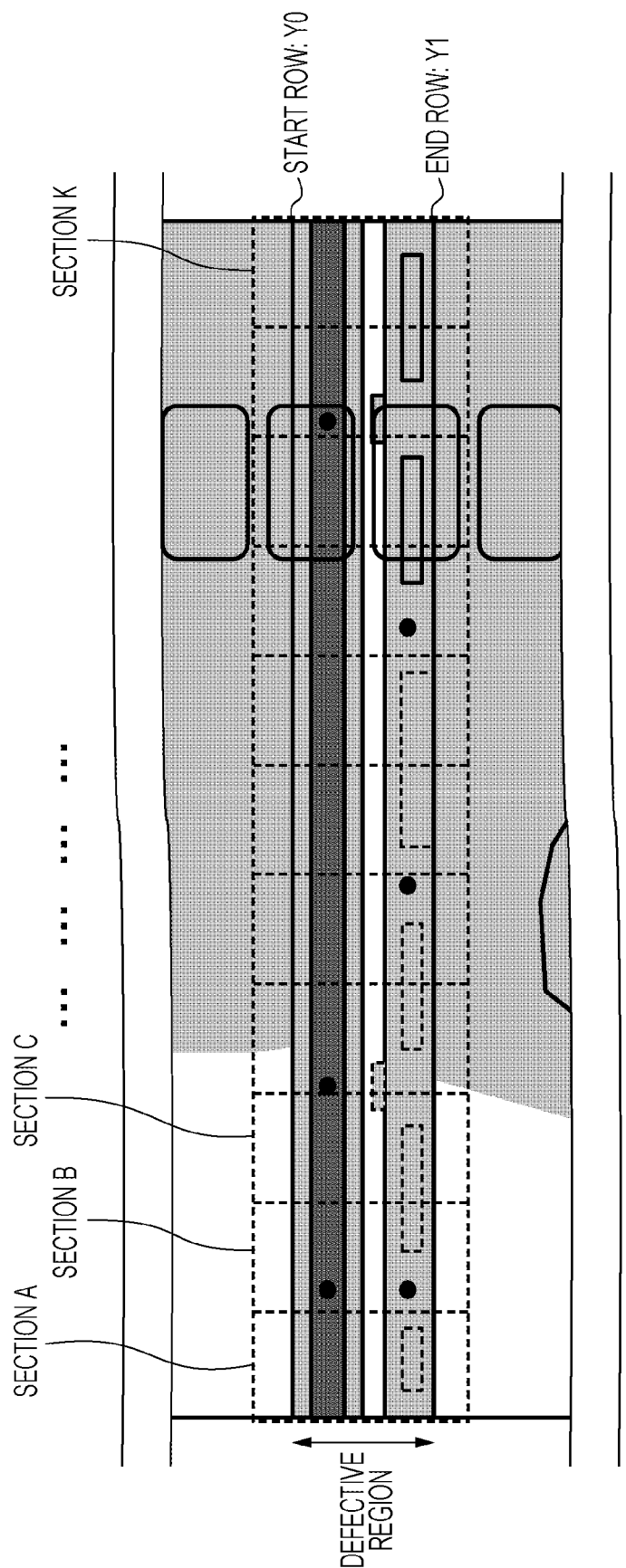
FIG. 7 is an illustration for explaining the position of a defective region in the first embodiment of the present invention.

Next, the image corrector 146 obtains information about the defective region targeted for correction in the composite image (S502). Specifically, the image corrector 146 obtains, as illustrated in FIG. 7, information about a start row Y0 and an end row Y1 of the defective region in the composite image as position information of the defective region. In the case in which a plurality of defective regions exist in a composite image as illustrated in (a) of FIG. 6, information about any one of the defective regions having not been corrected is obtained. For example, when neither the defective region 601 nor 603 has been subjected to correction, information about either of the defective regions 601 and 603 is obtained. When the defective region 601 has been subjected to correction but the defective region 603 has not been subjected to correction, information about the defective region 603 is obtained.

The image corrector 146 also obtains information about a start row Y2 and an end row Y3 of the defective region in structural data as information about the defective region and an identification code of the structural shadow. For example, in the case in which information about the defective region 601 in FIG. 6 is obtained, the information about the start row Y0 and the end row Y1 of the defective region 601 is obtained and the information about the start row Y2 and the end row Y3 of a corresponding defective region 602 in structural data is also obtained. The image corrector 146 also obtains 0x00 as the identification code of the structural shadow.

In the following description, a composite image before correction is indicated by I and structural data is indicated by P. In addition, the coordinate of the start rows Y0 and Y2 is 1 and the coordinate of the end rows Y1 and Y3 is H; the coordinates of an xth (1≤x≤W) point in a yth (1≤y≤H) faulty row are indicated as (x, y), the pixel value before correction corresponding to the coordinates is indicated as I(x, y), and the pixel value in structural data is indicated as P(x, y).

Next, the image corrector 146 checks the obtained identification code of the structural shadow (S503) and performs a correction operation in accordance with the identification code. This means that the image corrector 146 sets a correction method in accordance with the identification code. The correction method employed by the image corrector 146 varies between the case in which the identification code is 0x00 and the case in which the identification code is 0x01. In the case in which the identification code is 0x00, the image corrector 146 performs low-level correction for the composite image; by contrast, in the case of the identification code 0x01, the image corrector 146 performs high-level correction for the composite image. The low-level correction is suitable for an image of a simple structural shadow, whereas the high-level correction is suitable for an image of a complex structural shadow. The correction method differs because, if the high-level correction is performed for an image of a simple structural shadow, unnecessary correction may be performed, and as a result, image quality may be lowered. For example, the low-level correction includes at least either the correction according to a linear expression or the correction of one level; the high-level correction includes at least either the correction according to a polynomial expression or the correction of multiple levels. The image corrector 146 performs either the correction suitable for a composite image including a simple structural shadow or the correction suitable for a composite image including a complex structural shadow.

Specifically, in the case in which the identification code is 0x00, the image corrector 146 performs a correction operation suitable for a simple structural shadow as illustrated in (c) of FIG. 6 at which the amount of attenuation of radiation rays is relatively small (S504). More specifically, the image corrector 146 performs correction on the assumption that it is possible to model as the following equation a relationship among an image O without any structural shadow (that is, an image after an ideal correction operation), an image I before correction, and structural data P.

$$O(x,y) = I(x,y) - (a \cdot P(x,y) + b) \quad (1)$$

In the above equation, a and b are model parameters; the equation expresses a model on the assumption that a structural shadow represented as a linear expression regarding the structural data P covers the image I. The model parameters a and b are unknown and estimating optimum model parameters is therefore necessary. In this regard, in the present embodiment, optimum model parameters are estimated by solving an optimization problem based on the method of least squares. Specifically, the model parameters are calculated to satisfy the following equation while an error J is minimized.

$$J = \sum_{j=1}^{W} [O(j, y) - I(j, y) + (a \cdot P(j, y) + b)]^2 \quad (2)$$

In the above equation, the model parameters are estimated for each row by using a W number of pixel samples. In the above equation, the image O without any structural shadow is unknown. Thus, by using the fact that a high correlation exists between adjacent rows, data of an adjacent row without any structural shadow is used as an estimation value of the image O.

The adjacent row without any structural shadow exists only adjacent to the start row or the end row of a defective region. For this reason, the image corrector 146 performs estimation and correction of the model parameters such that the image corrector 146 successively corrects individual rows in order starting with the start row or the end row, in which a row after correction is used as an adjacent row without any structural shadow for a subsequent row.

Specifically, in the case in which correction is performed successively for individual rows in order starting with the start row, the image corrector 146 repeats estimation and correction of the model parameters in accordance with the following equations successively for individual rows in descending order starting with the start row (y=1) and ending with the end row (y=H).

$$(\hat{a}, \hat{b}) = \underset{(a,b)}{\mathrm{argmin}} \sum_{j=1}^{W} [O(j, y-1) - I(j, y) + (a \cdot P(j, y) + b)]^2 \quad (3)$$

$$O(x, y) = \begin{cases} I(x, y) - (\hat{a} \cdot P(x, y) + \hat{b}), & 1 \le y \le H \\ I(x, 0), & y = 0 \end{cases}$$

By contrast, in the case in which correction is performed successively for individual rows in order starting with the end row, the image corrector 146 repeats estimation and correction of the model parameters in accordance with the following equations successively for individual rows in ascending order starting with the end row (y=H) and ending with the start row (y=1).

$$(\hat{a}, \hat{b}) = \underset{(a,b)}{\mathrm{argmin}} \sum_{j=1}^{W} [O(j, y-1) - I(j, y) + (a \cdot P(j, y) + b)]^2 \quad (4)$$

$$O(x, y) = \begin{cases} I(x, y) - (\hat{a} \cdot P(x, y) + \hat{b}), & 1 \le y \le H \\ I(x, H+1), & y = H+1 \end{cases}$$

While only a correction result of either correction operation in one direction of the correction operations described above can be used, a correction result of the correction operation in the descending direction and a correction result of the correction in the ascending direction can be blended together. For example, when a correction result obtained by performing the correction operation in the descending direction is O1 and a correction result obtained by performing the correction operation in the ascending direction is O2, the correction results can be blended in consideration of weight based on the distance from the start row of correction as given by the equation indicated below. In this case, it is possible to reduce the effect of the error in the start row of correction on a subsequent row, and as a result, it is possible to perform correction with higher accuracy in comparison to the case of using only a correction result in one direction.

$$O(x, y) = \frac{H-y}{H-1} \cdot O1(x, y) + \frac{y-1}{H-1} \cdot O2(x, y) \quad (5)$$

In the above description, the case in which the identification code is 0x00, that is, the correction for the structural shadow illustrated in (c) of FIG. 6 is explained. Since the structural shadow illustrated in (c) of FIG. 6 has a structure that is simple and uniform in an X direction, it is possible to achieve sufficient correction accuracy by employing a low-level model such as a linear expression. Furthermore, since the structure is uniform in the X direction, estimating only a single pattern of model parameters for each row is necessary and this brings an advantage with respect to processing speed. If a high-level model is employed for a simple structure or if the model parameters are estimated for each pixel, deterioration of the shadow of an examinee is easily caused due to overfitting, and therefore, a low-level model is suitable.

Next, in the case in which the identification code is 0x01, the image corrector 146 performs a correction operation suitable for a complex structural shadow as illustrated in (d) of FIG. 6 at which the amount of attenuation of radiation rays is relatively large (S505). More specifically, the image corrector 146 performs correction on the assumption that it is possible to model as the following equation a relationship among the image O without any structural shadow (that is, an image after an ideal correction operation), the image I before correction, and the structural data P.

$$O(x, y) = I(x, y) - \left( \sum_{i=-2}^{2} \sum_{j=-2}^{2} a_{i,j} \cdot P(x+i, y+j) + b \right) \quad (6)$$

In the above equation, $a_{i,j}$ and b are model parameters; with the aim of making the equation suitable for a complex structural shadow, the number of model parameters are greater than that in the case in which the identification code is 0x00, and as a result, the flexibility of the model is increased. Moreover, by taking into account peripheral pixels in the structural data P, this model can reduce correction error caused by a slight geometric discrepancy between the image I and the structural data P. This can reduce omissions of correction caused by slight displacements of many edges that exist in a structural shadow.

The image corrector 146 estimates the model parameters $a_{i,j}$ and b by solving an optimization problem based on the method of least squares. Specifically, the model parameters are calculated to satisfy the following equation while an error J is minimized.

$$J = \sum_{k=1}^{W} \left[ O(k, y) - I(k, y) + \left( \sum_{i=-2}^{2} \sum_{j=-2}^{2} a_{i,j} \cdot P(k+i, y+j) + b \right) \right]^2 \quad (7)$$

Here, the adjacent-row data after correction is used as an estimation value of the image O in the above equation similarly to the case in which the identification code is 0x00; however, in the case of a structural shadow at which the amount of attenuation of radiation rays is relatively large, estimation accuracy may be deteriorated due to the effect of superposing noise included in data after correction. Thus, the average of adjacent-row data after correction is used as an estimation value.

Specifically, in the case in which correction is performed successively for individual rows in order starting with the start row, the image corrector 146 repeats estimation and correction of the model parameters in accordance with the following equations successively for individual rows in descending order starting with the start row (y=1) and ending with the end row (y=H).

$$(\hat{a}_{i,j}, \hat{b}) = \underset{(a_{i,j}, b)}{\text{argmin}} \quad (8)$$

$$\sum_{k=1}^{W} \left[ \frac{1}{N} \sum_{n=G}^{N-1} O(k, y-1-m) - I(j, y) + \left( \sum_{i=-2}^{2} \sum_{j=-2}^{3} a_{i,j} \cdot P(k+i, y+j) + b \right) \right]^2 O(x, y) =$$

$$\begin{cases} I(x, y) - \left( \sum_{i=-2}^{2} \sum_{j=-2}^{2} \hat{a}_{i,j} \cdot P(x+i, y+j) + \hat{b} \right), & 1 \le y \le H \\ I(x, y), & y \le 0 \end{cases}$$

In the above equation, N is the number of items of adjacent-row data after correction to be averaged and, for example, N=5.

By contrast, in the case in which correction is performed successively for individual rows in order starting with the end row, the image corrector 146 repeats estimation and correction of the model parameters in accordance with the following equations successively for individual rows in ascending order starting with the end row (y=H) and ending with the start row (y=1).

$$(\hat{a}_{i,j}, \hat{b}) = \underset{(a_{i,j}, b)}{\text{argmin}} \quad (9)$$

$$\sum_{k=1}^{W} \left[ \frac{1}{N} \sum_{n=G}^{N-1} O(k, y-1-m) - I(j, y) + \left( \sum_{i=-2}^{2} \sum_{j=-2}^{3} a_{i,j} \cdot P(k+i, y+j) + b \right) \right]^2 O(x, y) =$$

$$\begin{cases} I(x, y) - \left( \sum_{i=-2}^{2} \sum_{j=-2}^{2} \hat{a}_{i,j} \cdot P(x+i, y+j) + \hat{b} \right), & 1 \le y \le H \\ I(x, y), & y > H \end{cases}$$

In the equation, N is the number of items of adjacent-row data after correction to be averaged and, for example, N=5.

While the image corrector 146 may use only a correction result of either correction operation in one direction of the correction operations described above, the image corrector 146 may blend together a correction result of the correction operation in the descending direction and a correction result of the correction in the ascending direction. This correction operation is the same as the correction operation in the case of the identification code 0x00 and description thereof is thus not repeated.

While the image corrector 146 obtains a single pattern of the model parameters for each row in the above description, each row may be sectioned and the model parameters may be estimated for each section to perform correction. For example, each row is separated into sections A to K as illustrated in FIG. 7 and the estimation and correction of the model parameters as described above is performed for each section. Alternatively, the model parameters may be obtained for each pixel. For example, when the model parameters are estimated for the coordinates (x, y), the model parameters are estimated and corrected to satisfy the following equation in which the error J among some pixel samples close to each other in the same row is a minimum value.

$$J = \sum_{\Delta x=-N}^{N} \left[ \begin{array}{c} O(x+\Delta x, y) - I(x+\Delta x, y) + \\ \left( \sum_{i=-2}^{2} \sum_{j=-2}^{2} a_{i,j} \cdot P(x+\Delta x+i, y+j) + b \right) \end{array} \right]^2 \quad (10)$$

In the equation, N is a parameter that determines the number of samples used for estimating the model parameters. N can be set as any number in accordance with the goodness of fit of the model.

In the case in which the number of samples is relatively small, the result is easily affected by an outlier. Thus, the model parameters may be estimated by employing a robust estimation method such as M-estimation or least median of squares (LMedS) estimation.

In the above description, the case in which the model parameters are estimated for each section or each pixel is explained, and in this case, it is possible to reduce the effect of errors that may occur depending on the position. As a result, the model can be easily applied to a structure that considerably changes depending on the position, and thus, this correction method is suitable especially for a complex structural shadow.

Next, in the case in which the identification code is 0x01, the image corrector 146 further performs image correction for the defective region. As described above, since the amount of attenuation of radiation rays is relatively large at the complex structural shadow illustrated in (d) of FIG. 6, the granularity due to noise is increased. In this regard, the image corrector 146 performs a correction operation for a defective region to improve the granularity. This means that the image corrector 146 can determine, depending on the structural shadow of the radiation detection apparatus imaged in the composite image, whether to perform noise correction. While these specific examples should not be construed in the limiting sense, filtering by employing, for example, a smoothing filtering method, such as moving average or Gaussian smoothing, or a nonlinear filtering method that preserves edges, such as e filtering or bilateral filtering, can be utilized for noise correction, details of which is omitted as it is widely known.

Next, the image corrector 146 checks whether correction of the entire defective region has been completed (S506), and when the correction has been completed, the image corrector 146 ends the processing. When the correction has not been completed, the image corrector 146 returns to S502 and performs correction for a defective region that is newly set.

As described above, in the first embodiment, the radiographic system includes the plurality of radiation detection apparatuses that each detect radiation rays, the composition processor 142 that composites a plurality of radiographic images obtained from the plurality of radiation detection apparatuses and generates a composite image, and the image corrector 146 that corrects an area of the composite image, the area including the structure of a radiation detection apparatus, and that sets a correction method in accordance with a characteristic (the identification code) of the structural shadow of the imaged radiation detection apparatus. In this manner, the correction method is changed in accordance with the structural shadow of the radiation detection apparatus, and as a result, it is possible to perform correction suitable for the structural shadow.

It should be noted that, while in the present embodiment the composition processor 142 and the image corrector 146 are indicated as discrete configurations, compositing radiographic images and correcting an area including an imaged structure of a radiation detection apparatus may be performed together.

Second Embodiment

Figure 8:
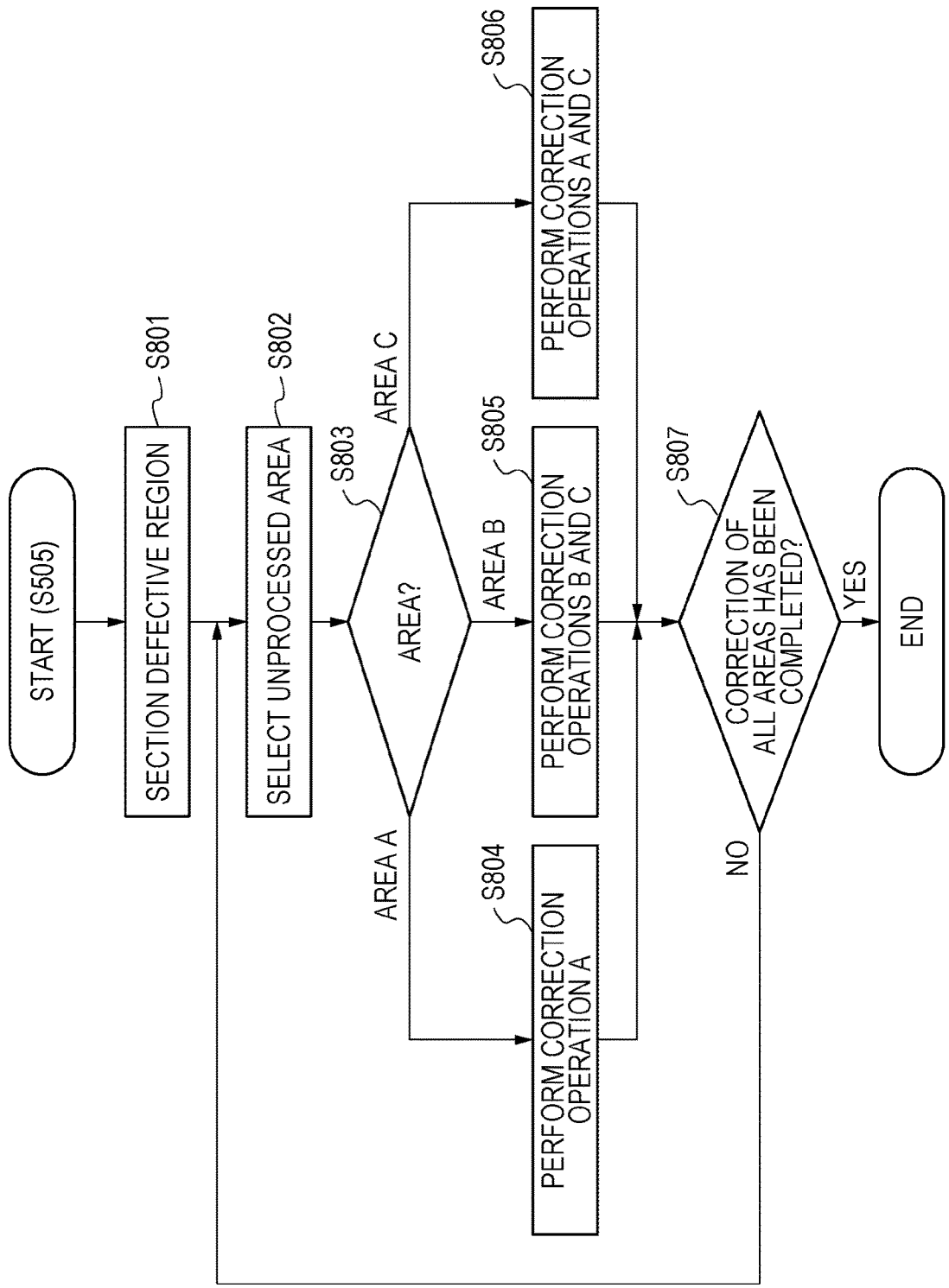
FIG. 8 is a flowchart illustrating a processing procedure of an image corrector of a second embodiment of the present invention.
Figure 9:
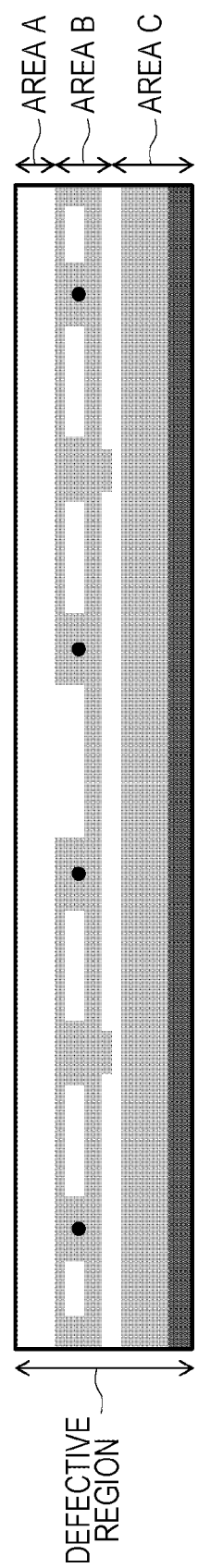
FIG. 9 is an illustration for explaining sectioning of a defective region in the second embodiment of the present invention.

Next, a second embodiment is described with reference to FIGS. 8 and 9. The point different from that of the first embodiment is to segment the defective region of a composite image in which a structural shadow of a radiation detection apparatus is imaged and to change the correction method with respect to each area. In the present embodiment, the image corrector 146 sections the area of a composite image including an imaged structure into subareas in accordance with variations of the structural shadow and sets a correction method for each subarea. Specifically, for example, the operation in S505 in FIG. 5 is performed by following a flow indicated by a flowchart in FIG. 8. The following description is given with reference to a flowchart in FIG. 8.

In the correction operation for the identification code 0x01 described in the first embodiment, the image corrector 146 sections a defective region into subareas in accordance with an imaged structural shadow (S801). In the present embodiment, the image corrector 146 performs sectioning in accordance with, for example, the complexity of the shape of the structural shadow and the amount of attenuation of radiation rays caused by the structure of the radiation detection apparatus. Specifically, the image corrector 146 performs sectioning into an area A, an area B, and an area C as illustrated in FIG. 9. The area A is an area of a simple structure at which the amount of attenuation of radiation rays is relatively small; the area B is an area of a complex structure at which the amount of attenuation of radiation rays is relatively large; and the area C is an area of a simple structure at which the amount of attenuation of radiation rays is relatively large. A particular manner of sectioning an area may be preset together with an identification code in accordance with the inner structure of a corresponding radiation detection apparatus.

Next, the image corrector 146 selects a particular subarea having not been corrected from the subareas (S802). The image corrector 146 determines which area the selected particular area is: the area A of a simple structure at which the amount of attenuation of radiation rays is relatively small, the area B of a complex structure at which the amount of attenuation of radiation rays is relatively large, or the area C is an area of a simple structure at which the amount of attenuation of radiation rays is relatively large (S803). Subsequently, a correction operation is performed in accordance with the characteristics of the determined area (S804 to S806).

For the area A of a simple structure at which the amount of attenuation of radiation rays is relatively small, the image corrector 146 performs the same correction operation as the correction operation described as S504 in the first embodiment (S804). For the area B of a complex structure at which the amount of attenuation of radiation rays is relatively large, the image corrector 146 performs the same correction operation as the correction operation described as S505 in the first embodiment (S805). To be specific, the image corrector 146 performs correction by employing a model of great flexibility and subsequently performs noise correction. The noise correction is, for example, a correction operation for improving the granularity as described in the first embodiment. For the area C of a simple structure at which the amount of attenuation of radiation rays is relatively large, the image corrector 146 performs the same correction operation as the correction operation described as S504 in the first embodiment and also performs noise correction (S806).

Next, the image corrector 146 checks whether correction of the all areas has been completed (S807). When the correction has been completed, the image corrector 146 ends the processing. When the correction has not been completed, the image corrector 146 returns to S802, selects an unprocessed area, and performs correction for the unprocessed area.

As described above, in the second embodiment, by segmenting a structural shadow and accordingly changing the correction method, it is possible to perform correction suitable for the case in which large variations exists in a structural shadow.

The present invention enables appropriate correction of composite images in the case in which radiation detection apparatuses of different inner structures exist together.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiographic system comprising:
   a plurality of radiation detection apparatuses that each detect radiation rays;
   a composition processor that composites a plurality of radiographic images obtained from the plurality of radiation detection apparatuses and generates a composite image; and
   an image corrector that corrects an area of the composite image, the area including an imaged structure of a radiation detection apparatus of the plurality of radiation detection apparatuses, and that sets a correction method in accordance with a characteristic of a structural shadow of the radiation detection apparatus imaged in the composite image.

2. The radiographic system according to claim 1, further comprising:
a memory unit that stores an identification code for identifying the structural shadow of the radiation detection apparatus imaged in the composite image, wherein
the image corrector sets the correction method in accordance with the identification code.

3. The radiographic system according to claim 2, wherein the identification code includes information indicating a type of the radiation detection apparatus.

4. The radiographic system according to claim 2, wherein the identification code includes position information of the radiation detection apparatus.

5. The radiographic system according to claim 1, wherein the image corrector performs either a correction operation suitable for the composite image in which the structural shadow indicates a simple structure or a correction operation suitable for the composite image in which the structural shadow indicates a complex structure.

6. The radiographic system according to claim 5, wherein when the correction operation suitable for the composite image in which the structural shadow indicates a complex structure is performed, the image corrector performs a correction operation for improving granularity with respect to the area including the imaged structure of the radiation detection apparatus.

7. The radiographic system according to claim 1, wherein in accordance with variations in the structural shadow, the image corrector sections the area including the imaged structure of the radiation detection apparatus into subareas and sets a correction method for each of the subareas.

8. The radiographic system according to claim 1, wherein the image corrector estimates a model parameter in a model that is set with respect to at least one pixel of the composite image and corrects a pixel value of the at least one pixel by using the estimated model parameter.

9. The radiographic system according to claim 8, wherein in accordance with the structural shadow of the radiation detection apparatus imaged in the composite image, the image corrector changes at least either the model or an estimation method for estimating the model parameter.

10. The radiographic system according to claim 1, wherein
in accordance with the structural shadow of the radiation detection apparatus imaged in the composite image, the image corrector determines whether to perform a noise-correction operation.

11. A radiographic system comprising:
a plurality of radiation detection apparatuses that each detect radiation rays;
a composition processor that composites a plurality of radiographic images obtained from the plurality of radiation detection apparatuses and generates a composite image;
a memory unit that stores an identification code for identifying a type and position information of a radiation detection apparatus of the plurality of radiation detection apparatuses; and
an image corrector that corrects, in accordance with the identification code, an area of the composite image, the area including an imaged structure of the radiation detection apparatus.

12. A radiographic method comprising:
compositing a plurality of radiographic images obtained from a plurality of radiation detection apparatuses that each detect radiation rays and generating a composite image; and
correcting an area of the composite image, the area including an imaged structure of a radiation detection apparatus of the plurality of radiation detection apparatuses, wherein
the correcting includes setting a correction method in accordance with a characteristic of a structural shadow of the radiation detection apparatus imaged in the composite image.

13. A radiographic method comprising:
compositing a plurality of radiographic images obtained from a plurality of radiation detection apparatuses that each detect radiation rays and generating a composite image;
storing an identification code for identifying a type and position information of a radiation detection apparatus of the plurality of radiation detection apparatuses; and
correcting, in accordance with the identification code, an area of the composite image, the area including an imaged structure of the radiation detection apparatus.

* * * * *